US010046058B2

(12) United States Patent
Rosendahl et al.

(10) Patent No.: US 10,046,058 B2
(45) Date of Patent: *Aug. 14, 2018

(54) USE OF HYDROPHOBIC ORGANIC ACIDS TO INCREASE HYDROPHOBICITY OF PROTEINS AND PROTEIN CONJUGATES

(71) Applicant: AntriaBio, Inc., Louisville, CO (US)

(72) Inventors: Mary S. Rosendahl, Broomfield, CO (US); Sankaram B. Mantripragada, Windsor, CO (US); Eliana B. Gomez, Boulder, CO (US)

(73) Assignee: REZOLUTE, INC., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,591

(22) Filed: Nov. 30, 2015

(65) Prior Publication Data

US 2016/0151510 A1 Jun. 2, 2016

Related U.S. Application Data

(60) Provisional application No. 62/086,294, filed on Dec. 2, 2014.

(51) Int. Cl.
| | |
|---|---|
| *A61K 9/16* | (2006.01) |
| *A61K 31/194* | (2006.01) |
| *A61K 38/00* | (2006.01) |
| *A61K 38/26* | (2006.01) |
| *A61K 38/27* | (2006.01) |
| *A61K 38/28* | (2006.01) |
| *A61K 47/48* | (2006.01) |
| *A61K 38/16* | (2006.01) |
| *A61K 38/29* | (2006.01) |
| *A61K 38/08* | (2006.01) |
| *A61K 9/00* | (2006.01) |
| *A61K 47/12* | (2006.01) |
| *A61K 9/50* | (2006.01) |
| *A61K 47/60* | (2017.01) |

(52) U.S. Cl.
CPC ...... *A61K 47/48215* (2013.01); *A61K 9/0019* (2013.01); *A61K 9/1647* (2013.01); *A61K 9/1682* (2013.01); *A61K 9/5031* (2013.01); *A61K 31/194* (2013.01); *A61K 38/08* (2013.01); *A61K 38/16* (2013.01); *A61K 38/26* (2013.01); *A61K 38/27* (2013.01); *A61K 38/28* (2013.01); *A61K 38/29* (2013.01); *A61K 47/12* (2013.01); *A61K 47/60* (2017.08)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 5,359,030 A | 10/1994 | Ekwuribe |
| 5,438,040 A | 8/1995 | Ekwuribe |
| 6,191,105 B1 | 2/2001 | Ekwuribe et al. |
| 6,323,311 B1 | 11/2001 | Liu et al. |
| 6,362,254 B2 | 3/2002 | Harris et al. |
| 6,437,025 B1 | 8/2002 | Harris et al. |
| 6,541,543 B2 | 4/2003 | Harris et al. |
| 6,599,627 B2 | 7/2003 | Yeo et al. |
| 6,620,413 B1 | 9/2003 | DeSauvage et al. |
| 6,664,331 B2 | 12/2003 | Harris et al. |
| 6,753,165 B1 | 6/2004 | Cox et al. |
| 6,774,180 B2 | 8/2004 | Kozlowski et al. |

(Continued)

FOREIGN PATENT DOCUMENTS

| | | |
|---|---|---|
| EP | 1049486 A1 | 11/2000 |
| EP | 2877158 A2 | 6/2015 |

(Continued)

OTHER PUBLICATIONS

Dalpiaz, et al., "Fabrication Via a Nonaqueous Nanoprecipitation Method, Characterization and In Vitro Biological Behavior of N6-Cyclopentyladenosine-Loaded Nanoparticles," "Pharmaceutical Nanotechnology," Published online Mar. 12, 2009 in Wiley InterScience_www.interscience.wiley.com.
Ashkenazi A, et al. Multifaceted action of Fuzeon as virus—cell membrane fusion inhibitor, Biochimica et Biophysica Acta, 1808, 2011, p. 2352-2358.
Bell S, et al.. Enhanced circulating half-life and antitumor activity of a site-specific pegylated interferon-alpha protein therapeutic, Bioconjugate Chem., vol. 19, 2008, p. 299-305.
Buckheit, R. W., et al. Potent and specific inhibition of HIV envelope-mediated cell fusion and virus binding by G quartet-forming oligonucleotide. AIDS Research and Human Retroviruses, 1994, vol. 10 (11), p. 1497-1506.

(Continued)

*Primary Examiner* — Kevin S Orwig
(74) *Attorney, Agent, or Firm* — Kilpatrick Townsend & Stockton LLP

(57) ABSTRACT

Examples may include a microsphere. The microsphere may include a biodegradable polymer. Furthermore, the microsphere may include a protein mixture selected from the group consisting of a protein-polyethylene glycol conjugate, the protein-polyethylene glycol conjugate and the hydrophobic anion of the organic acid, a protein and the hydrophobic anion of the organic acid, and combinations thereof. Examples may also include a method of making the microspheres. The method may further include reacting a polyethylene glycol with a protein to form a protein-PEG conjugate. In addition, the method may include protonating an amino group on the protein-PEG conjugate with a hydrophobic organic acid to form the protein-PEG conjugate salt. Furthermore, the method may include mixing the protein-PEG conjugate salt in an organic solvent with a biodegradable polymer. The method may also include emulsifying the mixture. Additionally, the method may include hardening the emulsified mixture into the controlled-release microspheres.

16 Claims, 11 Drawing Sheets

(56) References Cited

U.S. PATENT DOCUMENTS

| | | | |
|---|---|---|---|
| 7,049,415 | B2 | 5/2006 | Bailon et al. |
| 7,053,150 | B2 | 5/2006 | Kozlowski et al. |
| 7,223,803 | B2 | 5/2007 | Harris et al. |
| 7,528,202 | B2 | 5/2009 | Harris et al. |
| 7,557,183 | B2 | 7/2009 | DiMarchi et al. |
| 7,714,088 | B2 | 5/2010 | Harris et al. |
| 7,834,138 | B2 | 11/2010 | Kozlowski et al. |
| 7,910,661 | B2 | 3/2011 | Kozlowski et al. |
| 8,003,742 | B2 | 8/2011 | Harris et al. |
| 8,084,572 | B2 | 12/2011 | Kozlowski et al. |
| 8,183,340 | B2 | 5/2012 | Glaesner et al. |
| 8,202,540 | B1* | 6/2012 | Muller ............... A61K 9/14 424/114 |
| 8,338,368 | B2 | 12/2012 | DiMarchi et al. |
| 8,378,073 | B2 | 2/2013 | Heywood |
| 8,383,380 | B2 | 2/2013 | Kozlowski et al. |
| 8,617,531 | B2 | 12/2013 | Cox et al. |
| 8,633,300 | B2 | 1/2014 | Ostergaard et al. |
| 8,710,001 | B2 | 4/2014 | Madsen et al. |
| 8,722,032 | B2 | 5/2014 | Kozlowski et al. |
| 8,729,017 | B2 | 5/2014 | DiMarchi et al. |
| 9,040,658 | B2 | 5/2015 | Kozlowski et al. |
| 2002/0155158 | A1* | 10/2002 | Lewis ............... A61K 47/482 424/486 |
| 2004/0181035 | A1* | 9/2004 | Kinstler ........... A61K 47/48215 530/350 |
| 2005/0048123 | A1 | 3/2005 | Su et al. |
| 2005/0277586 | A1 | 12/2005 | Taguchi et al. |
| 2006/0100144 | A1 | 5/2006 | Lang et al. |
| 2006/0228414 | A1 | 10/2006 | Cook |
| 2007/0083006 | A1 | 4/2007 | Hinds et al. |
| 2008/0026068 | A1 | 1/2008 | Brown et al. |
| 2008/0026444 | A1 | 1/2008 | Takakura et al. |
| 2008/0069865 | A1 | 3/2008 | Southard et al. |
| 2009/0239790 | A1 | 9/2009 | Pool et al. |
| 2010/0016550 | A1 | 1/2010 | Dong et al. |
| 2012/0178914 | A1 | 7/2012 | Henderson et al. |
| 2012/0201873 | A1 | 8/2012 | Hohlbaum et al. |
| 2012/0208258 | A1 | 8/2012 | Lee et al. |
| 2012/0329127 | A1 | 12/2012 | Siekmann et al. |
| 2014/0120120 | A1 | 5/2014 | Woo et al. |

FOREIGN PATENT DOCUMENTS

| | | | |
|---|---|---|---|
| KR | 20060029770 A | 4/2006 | |
| KR | 20120043205 A | 5/2012 | |
| WO | WO 01/03670 * | 1/2001 | ............... A61K 9/14 |
| WO | 2004022004 A2 | 3/2004 | |
| WO | 2005002625 A2 | 1/2005 | |
| WO | 2005009357 A2 | 2/2005 | |
| WO | 2007084460 A2 | 7/2007 | |
| WO | 2009069983 A2 | 6/2009 | |
| WO | 2011038900 A2 | 4/2011 | |
| WO | 2011163473 A1 | 12/2011 | |
| WO | 2012054861 A1 | 4/2012 | |
| WO | 2012054882 A1 | 4/2012 | |
| WO | 2012155780 A1 | 11/2012 | |
| WO | 2015038938 A1 | 3/2015 | |
| WO | 2015095406 A1 | 6/2015 | |

OTHER PUBLICATIONS

Chang D, et al. Bioanalytical method development and validation for a large peptide HIV fusion inhibitor (Enfuvirtide or T-20) and its metabolite in human plasma using LC-MS/MS, Journal of Pharmaceutical and Biomedical Analysis, 2005, vol. 38, p. 487-496.

Dutheil D, et al. Polyethylene glycols interact with membrane glycerophospholipids: is this part of their mechanism for hypothermic graft protection?, Journal of Chemical Biology, 2009, vol. 2(1), p. 39-49.

Fee, C. Size-exclusion reaction chromatography: A new technique for protein PEGylation, Biotechnology and Bioengineering, Apr. 20, 2003, vol. 82(2), p. 200-206.

Foy K, et al. Enfuvirtide (T-20): potentials and challenges, Journal of the Association of Nurses in AIDS Care, Nov./Dec. 2004, vol. 15 (6), p. 65-71.

Geitmann, M. et al. Biosensor-Based Kinetic Characterization of the Interation between HIV-1 Reverse Transcriptase and Non-nucleoside Inhibitors, Journal of Medical Chemistry, 2006, vol. 49, p. 2367-2374.

Harris JM, et al. Pegylation: A novel process for modifying pharmacokinetics, Clinical Pharmacokinetics, 2001, vol. 40(7), p. 539-551.

Harris JM and Chess RB. Effect of Pegylation on pharmaceuticals, Nature Reviews: Drug Discovery, Mar. 2003, vol. 2, p. 214-221.

Huet T, et al. Long-lasting enfuvirtide carrier pentasaccharide conjugates with potent anti-human immunodeficiency virus Type 1 activity. Antimicrobial Agents and Chemotherapy, Jan. 2010, vol. 54(1), p. 134-142.

Ingallinella, P, et al. Addition of a cholesterol group to an HIV peptide fusion inhibitor dramatically increases its antiviral potency, PNAS, Apr. 7, 2009, vol. 106 (14), p. 5801-5806.

Katre NV. Immunogenicity of recombinant IL-2 modified by covalent attachment of polyethylene glycol, The Journal of Immunology, Jan. 1, 1990, vol. 144 (1), pp. 209-213.

Katre NV, et al. Chemical modification of recombinant interleukin-2 by polyethylene glycol increases its potency in the murine Meth A sarcoma model, Proceedings of the National Academy of Sciences USA, Biochemistry, Mar. 1987, vol. 84, pp. 1487-1491.

Keating MJ, et al. L-asparaginase and PEG asparaginase—past, present, and future, Leukemia & Lymphoma, vol. 10, 1993, pp. 153-157.

McNeely, T.B., Inhibition of HIV Type I infectivity by SLPI occurs prior to viral reverse transcription, Blood, Aug. 1, 1990, vol. 90 (3), pp. 1141-1149.

McKinnel JA , et al. Novel drug classes: entry inhibitors [enfuvirtide, chemokine (C-C motif) receptor 5 antagonists], Current Opinion in HIV and AIDS, 2009, vol. 4, pp. 513-517.

Moore JP, et al. The entry of entry inhibitors: A fusion of science and medicine, PNAS, Sep. 16, 2003, vol. 100(19), pp. 10598-10602.

Moreno S, et al. The future of antiretroviral therapy challenges and needs, The Journal of Antimicrobial Chemotherapy, 2010, vol. 65, pp. 827-835.

Pang W, et al. Current peptide HIV type-1 fusion inhibitors, Antiviral Chemistry & Chemotherapy, 2009, vol. 20, pp. 1-18.

Rosendahl MS, et al. A long-acting, highly potent interferon alpha-2 conjugate created using site-specific PEGylation, Bioconjugate Chemistry, 2005, vol. 16, pp. 200-207.

Stoddart CA, et al. Albumin-conjugated C34 peptide HIV-1 fusion inhibitor: equipotent to C34 and T-20 in vitro with sustained activity in SCID-hu THY/LIIV mice, The Journal of Biological Chemistry, Dec. 5, 2008, vol. 283(49), pp. 34045-34052.

Tuma R, et al. Solution conformation of the extracellular domain of the human TNF receptor probed by Raman and UV resonance Raman Spectroscopy. Structural effects of an engineered PEG Linker, Biochemistry, 1995, vol. 34, pp. 15150-15156.

Zhu Y, et al. Identification of a gp41 core-binding molecule with homologous sequence of human TNNI3K-like protein as a novel human immunodeficiency virus type 1 entry inhibitor., Journal of Virology, Sep. 2010, vol. 84(18), pp. 9359-9368.

Clark R, et al. Long-acting growth hormones produced by conjugation with polyethylene glycol. The Journal of Biological Chemistry, Sep. 6, 1996, vol. 271(36), p. 21969-21977.

Grace MJ, et al. Site of pegylation and polyethylene glycol molecule size attenuate interferon-alpha antiviral and antiproliferative activities through the JAK/STAT signaling pathway, The Journal of Biological Chemistry, Feb. 25, 2005, vol. 280(8), pp. 6327-6336.

Veronese FM, et al. Site-specific pegylation of G-CSF by reversible denaturation, Bioconjugate Chemistry, 2007, vol. 18, p. 1824-1830.

Kumar L, et al. Salt Selection in Drug Development, Pharmaceutical Technology, Mar. 2, 2008, Retrieved Nov. 25, 2014 from http://license.icopyright.net/user/viewFreeUse.act?fuid=MTg2OTc5Njc%3D, 18 pages.

Van Der Walle, C. F., et al. Current approaches to stabilising and analysing proteins during microencapsulation in PLGA, Expert Opinion on Drug Delivery, vol. 6:2, 2009, p. 177-186.

(56) References Cited

OTHER PUBLICATIONS

Rosenfeld R.G., Bakker B. 2008. Compliance and persistence in pediatric and adult patients receiving growth hormone therapy. Endocrine Practice, Mar. 2008, vol. 14(2), p. 143-154.

Wyatt, Philip, "Light scattering and the absolute characterization of macromolecules," Analytica Chimica Acta, vol. 272, Issue 1, Feb. 1, 1993_pp. 1-40. Retrieved from: http://mmrc.caltech.edu/PD_Expert/Intros/Light%20Scattering%20and%20MW.pdf.

International Preliminary Report on Patentability of PCT/US2015/063102 dated Jun. 15, 2017, all pages.

* cited by examiner

USE OF HYDROPHOBIC ORGANIC ACIDS TO INCREASE HYDROPHOBICITY OF PROTEINS AND PROTEIN CONJUGATES

CROSS-REFERENCE TO RELATED APPLICATION

This application claims the benefit of priority to U.S. Provisional Application No. 62/086,294, filed Dec. 2, 2014. This application is related to U.S. application Ser. No. 14/954,701, entitled "PROTEINS AND PROTEIN CONJUGATES WITH INCREASED HYDROPHOBICITY," filed Nov. 30, 2015. The content of these applications is incorporated herein by reference for all purposes.

BACKGROUND

Delivery of a drug, hormone, protein, or other medically active agent into a patient faces a number of challenges. The medically active agent has to be delivered into the patient. Two such ways are ingestion and injection. With ingestion the drug may have to pass through a patient's digestive system before reaching the bloodstream or targeted area for treatment. Injection may allow the medically active agent to reach the bloodstream or targeted area for treatment quickly or directly, but injection may be inconvenient or painful for the patient. Once in the body, the concentration of the medically active agent as a function of time may vary depending on the type of medically active agent, the attachment of different functional groups or molecules on the medically active agent, the encapsulation of the medically active agent, or other factors. If the concentration of the medically active agent decreases below a threshold, the medically active agent may need to be administered once again. Many medically active agents have to be administered frequently, including several times a day. A more frequent administration schedule may increase the inconvenience to the patient, may decrease the compliance rate by patients, and may lead to less than optimal outcomes for the patient. If the medically active agent is administered by injection, another injection increases the frequency of pain, the risk of infection, and the probability of an immune response in the patient. Thus, a need for medically active agents that have superior concentration profiles in the patient exists. The methods and compositions described herein provide solutions to these and other needs.

BRIEF SUMMARY

A medically active agent may be attached to an aliphatic chain, a polyethylene glycol (PEG), a hydrophobic anion, or other compounds. The attachment of the polyethylene glycol may add molecular weight to the medically active agent and may lead to an increased half-life of the medically active agent. Additionally, the attachment of polyethylene glycol, including smaller PEG molecules, or a hydrophobic anion to a medically active agent may increase the hydrophobicity of the medically active agent and may make the medically active agent amphiphilic. The medically active agent may be more easily dissolved in an organic solvent with a biodegradable polymer. The biodegradable polymer may encapsulate the medically active agent in a microsphere. The encapsulation of the medically active agent may increase the half-life of the medically active agent. The formulations described herein may release the medically active agent slowly and uniformly over a period of time. The release profile may result in a sustained and near peak-less protein level over the intended treatment period, without the need of an excipient. The resulting concentration profile of the medically active agent in a patient may lead to a more optimal clinical result in the patient. Formulations described herein may be administered to a patient as infrequently as once a month. Processes to manufacture these formulations may be efficient, high yielding, or not prohibitively expensive.

Examples may include a method of making a protein-PEG conjugate salt with increased hydrophobicity. The method may include providing an aqueous protein solution. This aqueous protein solution may include a protein and a pH buffer. The method may also include reacting a polyethylene glycol with the protein to form a protein-PEG conjugate. The method may further include protonating an amino group on the protein-PEG conjugate with a hydrophobic organic acid. The protonation may occur in an organic phase. The protonation may form the protein-PEG conjugate salt having a hydrophobic anion that increases the hydrophobicity-PEG conjugate salt.

Examples may include a method of making a protein-PEG conjugate with increased hydrophobicity. The method may include providing an aqueous protein solution, which may include a protein and a pH buffer. The method may further include reacting a polyethylene glycol with the protein to form a protein-PEG conjugate. The protein-PEG conjugate may have a higher hydrophobicity than the protein.

Examples may include a method of making a protein salt with increased hydrophobicity. The method may include providing an aqueous protein solution with a protein and a pH buffer. The method may further include protonating at least one amino group on the protein with a hydrophobic organic acid. The protonation may form the protein salt having a hydrophobic anion that increases the hydrophobicity of the protein salt.

In examples, a method of making controlled-release microspheres containing a protein-PEG conjugate salt may include providing an aqueous protein solution. The aqueous protein solution may include a protein and a pH buffer. The method may further include reacting a polyethylene glycol with the protein to form a protein-PEG conjugate. In addition, the method may include protonating an amino group on the protein-PEG conjugate with a hydrophobic organic acid. The protonation may form the protein-PEG conjugate salt having a hydrophobic anion. Furthermore, the method may include mixing the protein-PEG conjugate salt in an organic solvent with a biodegradable polymer. The hydrophobic anion of the protein-PEG conjugate salt may increase the solubility of the salt in the organic solvent. The method may also include emulsifying the mixture of the protein-PEG conjugate salt and the biodegradable polymer in an aqueous solution. Additionally, the method may include hardening the emulsified mixture of the protein-PEG conjugate salt and the biodegradable polymer into the controlled-release microspheres.

Examples may include a microsphere. The composition may include a biodegradable polymer. Furthermore, the microsphere may include a protein mixture selected from the group consisting of a protein-polyethylene glycol conjugate, the protein-polyethylene glycol conjugate and the hydrophobic anion of the organic acid, a protein and the hydrophobic anion of the organic acid, and combinations thereof.

Examples may also include a composition that may include a biodegradable polymer, an organic solvent, and a protein mixture. The protein mixture may include a protein, a protein-polyethylene glycol conjugate, a hydrophobic anion of an organic acid, or combinations thereof. The composition may be a solution or a suspension.

In examples, methods may include making a solution or suspension of a biodegradable polymer and a protein-PEG conjugate salt. The methods may include providing a protein-PEG conjugate. The protein-PEG conjugate may be free of the protein-PEG conjugate salt. The methods may also include mixing the biodegradable polymer, the protein-PEG conjugate, a hydrophobic organic acid, and an organic solvent in a mixture. Methods may include forming the protein-PEG conjugate salt, which may include the protein-PEG conjugate and an anion of the hydrophobic organic acid. Additionally, methods may include agitating the mixture to form the solution or suspension.

Some examples may include methods of making a solution or suspension of a biodegradable polymer and a protein-PEG conjugate salt. The methods may include dissolving a biodegradable polymer in an organic solvent to form a mixture. The methods may also include adding the protein-PEG conjugate and a hydrophobic organic acid to the mixture. The methods may further include protonating an amino group on the protein-PEG conjugate with the hydrophobic organic acid. The protonation may form the protein-PEG conjugate salt having a hydrophobic anion. Furthermore, the methods may include agitating the mixture to form the solution or suspension.

The examples described herein may provide for a superior concentration profile. The protein may retain its activity after PEGylation and encapsulation. The protein may have a low burst release in vitro, in vivo, and/or in situ. The concentration release may have a near zero order kinetic profile, with the concentration release varying little with time or the concentration of medically active agent left in the microsphere. The protein may be essentially completely released from the microsphere when administered to the patient.

BRIEF DESCRIPTION OF THE DRAWINGS

The present technology is described in conjunction with the appended figures.

DETAILED DESCRIPTION

Figure 1:
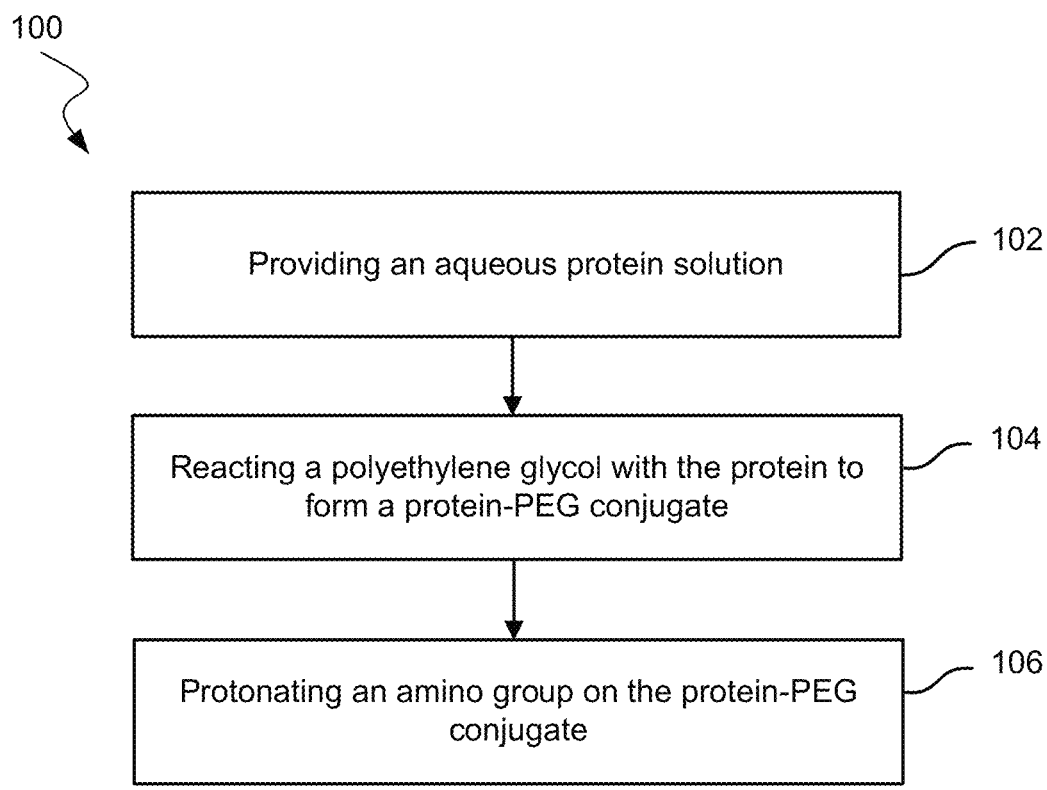
FIG. 1 shows a block diagram of a method of making a protein-PEG conjugate salt with increased hydrophobicity according to examples.

Medically active agents that may need to be administered to a patient include drugs, hormones, and proteins. One such protein is human growth hormone. Human growth hormone (hGH), a 191 amino acid peptide, is a hormone that increases cell growth and regeneration. hGH may be used to treat growth disorders and deficiencies. For instance, hGH may be used to treat short stature in children or growth hormone deficiencies in adults. Conventional methods of administering hGH include daily subcutaneous injection. A study[1] has shown that most patients are only occasionally compliant or non-compliant with their hGH treatments.

[1] Rosenfeld R. G., Bakker B. 2008. Compliance and persistence in pediatric and adult patients receiving growth hormone therapy. *Endocr. Pract.* 14(2): 143-154.

Another protein that may be used as a medically active agent is glucagon-like peptide-1 (GLP-1). GLP-1, a 31 amino acid peptide, is an incretin, a hormone that can decrease blood glucose levels. GLP-1 may affect blood glucose by stimulating insulin release and inhibiting glucagon release. GLP-1 also may slow the rate of absorption of nutrients into the bloodstream by reducing gastric emptying and may directly reduce food intake. The ability of GLP-1 to affect glucose levels has made GLP-1 a potential treatment for type 2 diabetes and other afflictions. In its unaltered state, GLP-1 has an in vivo half-life of less than two minutes as a result of proteolysis. GLP-1 receptor agonist treatments can be improved by minimizing side effects, increasing effectiveness, and extending the duration of the effect.

Conventional treatment of diabetes and other afflictions may result in side effects. Such side effects may include hypoglycemia, weight gain, an immune response, inflammation of the pancreas, increased risk of thyroid cancer, nausea, or pain related to injection of a treatment. In addition, conventional treatment may fail to achieve the target glycaemia in diabetic patients. Certain formulations may result in an uneven administration of the protein to the patient, which may include an initial burst of the drug. The process of formulating the protein into an administrable treatment may also result in denaturation or aggregation. The process of manufacturing an effective formulation may have high costs or low yields.

Similar to hGH and GLP-1, enfuvirtide (Fuzeon®) is a medically active agent that may face challenges when administered to patients. Enfuvirtide may help treat HIV and AIDS. However, enfuvirtide may have to be injected subcutaneously twice a day. Injections may result in skin sensitivity reaction side effects, which may discourage patients from continuing use of enfuvirtide. A enfuvirtide treatment with less frequent administrations or extended duration may be needed to increase patient compliance, lower cost, and enhance the quality of life for patients with HIV and AIDS.

Another medically active agent is parathyroid hormone (PTH) or a fragment of PTH. PTH is an anabolic (bone forming) agent. PTH may be secreted by the parathyroid glands as a polypeptide containing 84 amino acids with a molecular weight of 9,425 Da. The first 34 amino acids may be the biologically active moiety of mineral homeostasis. A synthetic, truncated version of PTH is marketed by Lilly as Forteo® Teriparatide. PTH or a fragment of PTH may be used to treat osteoporosis. Teriparatide may often be used after other treatments as a result of its high cost and required daily injections. As with other medically active agents, a PTH treatment with less frequent administrations or extended duration may be desired.

Unaltered proteins may not have the desired concentration profiles and other favorable characteristics. PEGylation, the process of attaching polyethylene glycol to a molecule, can aid in the administration of peptides and proteins, which may lead to improved pharmacological properties and increased effectiveness. PEG is a linear polymer composed of subunits of ethylene glycol and is soluble in both water and many organic solvents. PEG is flexible, biocompatible, and non-toxic. As a result of PEG properties, PEGylation may increase half-life and/or solubility of a protein or peptide. PEG may be attached to a monomethoxy group. The PEG may be a polyethylene glycol aldehyde, including a methoxy polyethylene glycol aldehyde.

Another way of altering the concentration profile of a medically active agent may be to encapsulate the medically active agent in a biodegradable material. As the material degrades gradually in the patient, the medically active agent may be released gradually. The process of encapsulating the medically active agent may include an organic solvent. The medically active agent may be hydrophilic and insoluble in the organic solvent. The hydrophobicity of the medically active agent may be increased to facilitate encapsulation.

To increase the hydrophobicity of the medically active agent, the medically active agent may be PEGylated. Not all medically active agents will increase in solubility and retain their biological activity when PEGylated. For example, small PEG molecules may not be enough to enhance the solubility of a protein. Adding longer chain PEG molecules may eventually increase the hydrophobicity and solubility of the protein, but these longer chains may be too large relative to the protein and compromise the protein's biological activity. As an example, increasing the PEGylation with hGH was found to linearly reduce the affinity of hGH for its receptor.[2] Additionally, PEGylation of interferon-α (IFN-α) may result in lower in vitro specific activity, depending on the site of PEGylation and the size of the PEG molecule.[3] Furthermore, PEGylation may not increase solubility. For instance, a PEG-insulin conjugate with a small PEG molecule of 2,000 Daltons may not be adequately soluble in organic solvents. As another example, PEGylation of granulocyte colony stimulating factor (G-CSF) was discovered to increase aggregation of G-CSF and to lower solubility.[4]

[2] Clark R. et al. 1996. Long-acting growth hormones produced by conjugation with polyethylene glycol. *J. Biol. Chem.* 217: 21969-21977.
[3] Grace M. J. et al. 2005. Site of pegylation and polyethylene glycol molecule size attenuate interferon-alpha antiviral and antiproliferative activities through the JAK/STAT signaling pathway. *J. Biol. Chem.* 280: 6327-6336.
[4] Veronese F. M. et al. 2007. Site-specific pegylation of G-CSF by reversible denaturation. *Bioconjug. Chem.* 18(6): 1824-30.

Alternatively, the hydrophobicity may be increased by attaching a hydrophobic ion to the medically active agent. As with PEGylation, attaching a hydrophobic anion to the medically active agent does not necessarily increase the hydrophobicity of all medically active agents. A protein may not have or may not form enough positively charged sites to pair with hydrophobic anions. The number of anions attached to the protein and also the increase in hydrophobicity may then be limited. For example, acidic proteins such as serum albumins may contain more acidic amino acids than basic amino acids. Such acidic proteins may not be easily protonated by hydrophobic acids.

The combination of PEGylation and attaching a hydrophobic ion to a medically active agent may produce synergistic results where the hydrophobicity of the medically active agent increases more with the combination than what may be expected from the sum of the increased hydrophobicities resulting from PEGylation alone and from attaching a hydrophobic ion alone. A protein may achieve superior outcomes in a patient if the protein is made into a protein-PEG conjugate salt.

As shown in FIG. 1, examples of the present technology may include a method 100 of making a protein-PEG conjugate salt with increased hydrophobicity. The method may include providing an aqueous protein solution 102. This aqueous protein solution may include a protein and a pH buffer. The pH buffer may include an inorganic salt of phosphoric acid.

The protein may have a molecular weight of 3,000 Daltons or more, between 3,000 Daltons and 10,000 Daltons, 10,000 Daltons or more, between 10,000 Daltons and 15,000 Daltons, 15,000 Daltons or more, between 15,000 Daltons and 20,000 Daltons, or 20,000 Daltons or more according to examples. In these or other examples, the protein may include 30 amino acid units or more, between 30 amino acid units and 100 amino acid units, 100 amino acid units or more, between 100 amino acid units and 150 amino acid units, or 150 amino acid units or more. The protein may include human growth hormone, glucagon-like peptide-1 (GLP-1), insulin, parathyroid hormone, a fragment of parathyroid hormone, enfuvirtide (Fuzeon®), or octreotide (Sandostatin®) in examples. GLP-1 may be a natural extract or synthetic. The protein may include analogs or derivatives of GLP-1. A combination of proteins may be included in the aqueous solution. For example, both GLP-1 and insulin may be included in the aqueous solution.

Method 100 may include reacting polyethylene glycol with the protein to form a protein-PEG conjugate 104. The reaction of the PEG with the protein may form a protein-PEG conjugate at an N-terminus of the protein.

The reaction of the polyethylene glycol with the protein may form a protein-PEG conjugate with PEG at specific cysteine sites, or the reaction may not result in any or substantially any protein-PEG conjugates with PEG at specific cysteine sites. The reaction of the PEG with the protein may include forming at least one of an amine bond, an amide bond, an ester bond, or a disulfide bond between the PEG and the protein. The reaction may exclude the formation of any bond or groups of bonds. The bonds may form with the reactive group at the end of the PEG polymer.

Reacting the polyethylene glycol with the protein may include attaching a thiol-reactive PEG to a cysteine residue of a protein. Thiol-reactive PEGs may include different reactive groups, which may include maleimide and vinylsulfone. Thiol-reactive PEGs may have a molecular weight from 2 to 40 kDa. PEGylation reactions with thiol-reactive PEGs may be at a neutral pH. Cysteine residues in some proteins may participate in disulfide bonds and may not be available for derivatization. Through in vitro site-directed mutagenesis techniques, an additional cysteine residue can be introduced at any specific site on the protein. An additional cysteine residue may serve as a site for the attachment of a PEG molecule. Using these additional cysteine residues may avoid product heterogeneity and loss of activity that may result from random amine PEGylation reactions.

In these or other examples, the polyethylene glycol may have a molecular weight of 5,000 Daltons or less or 2,000 Daltons or less. A larger polyethylene glycol may increase the half-life of the protein. A smaller polyethylene glycol may increase the solubility of the protein-PEG conjugate without a long half-life. For example, a polyethylene glycol with a molecular weight of 2,000 Daltons may have a half-life of less than an hour. A smaller polyethylene glycol or PEG may be used to increase the solubility of the protein-PEG conjugate, with the encapsulation of the protein achieving most of the desired increase in half-life. Method 100 may not include reacting a polyethylene glycol ester with the protein. A polyethylene glycol may be selective for primary amines, while the polyethylene glycol ester may react with other functionalities and amino acids.

Method 100 may also include protonating an amino group on the protein-PEG conjugate 106 with a hydrophobic organic acid. Protonating the amino group may occur in an organic phase and not an aqueous phase. The molar ratio of the hydrophobic organic acid to the protein-PEG conjugate may range from 1:1 to 11:1, from 1:1 to 5:1, from 5:1 to 11:1, from 1:1 to 2:1, or from 3:1 to 8:1 according to examples. The protonation may form the protein-PEG conjugate salt having a hydrophobic anion that increases the hydrophobicity-PEG conjugate salt. The protein-PEG conjugate salt may include a monoPEGylated salt. The hydrophobic organic acid may include pamoic acid, docusate hydrogen, furoic acid, or mixtures thereof. Organic acids may include carboxylic acids, sulfonic acids, alcohols, or organic compounds with thiol groups. The hydrophobic organic acid may exclude any acid described or any groups of acids described.

The hydrophobic anion may include anions associated with the hydrophobic organic acids. For example, the hydrophobic anion may include a pamoate anion, a docusate anion, or a furoate anion. In these or other examples, the hydrophobic anion may be a fatty acid anion, a phospholipid anion, a polystyrene sulfonate anion, or mixtures thereof. The phospholipid of the phospholipid anion may include phosphatidylcholine, phosphatidylglycerol, phosphatidylserine, phosphatidylinositol, phosphatidylethanolamine, phosphocholine, or mixtures thereof. The hydrophobic anion may also exclude any anion described or any group of anions described. The hydrophobic anion may attach to a specific side chain on the protein or it may attach to multiple side chains on the protein. The hydrophobic anion may have a log P greater than 1. The log P is the water-octanol partition coefficient and may be defined as the logarithm of the concentration of the protein salt in octanol to the concentration of the protein salt in water. A log P greater than 1 may result in a concentration in octanol that is 10 times greater than that in water. The water-octanol partition coefficient may be useful in comparing different molecules for their ability to partition into a hydrophobic phase, when the molecules themselves may be amphipathic. Methods may also include adding cationic detergents, such as dodecylamine hydrochloride or cetyltrimethylammonium bromide (CTAB), which may counter the charge of negatively charged peptides and may increase the hydrophobicity.

Figure 2:
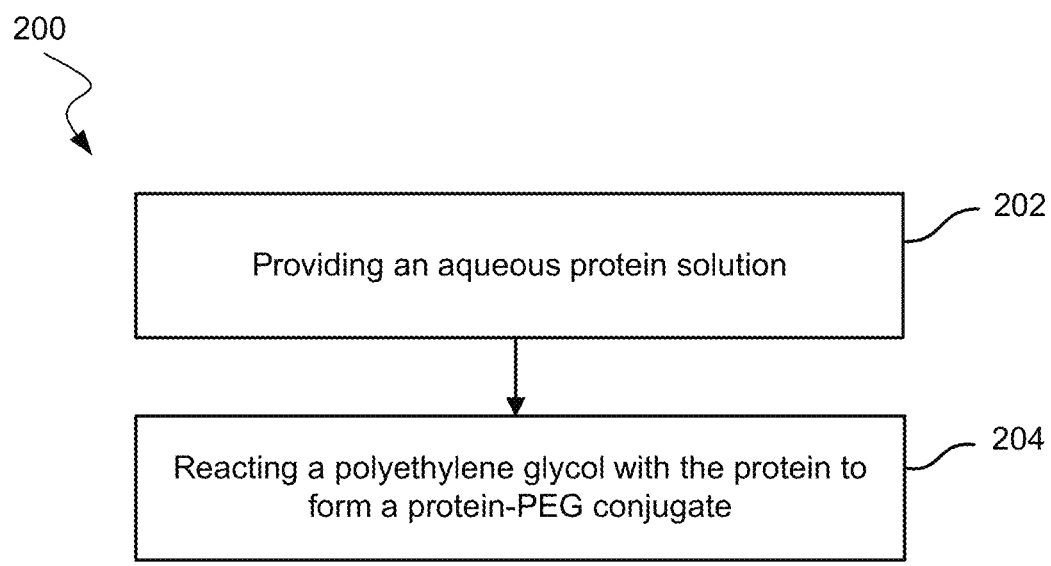
FIG. 2 shows a block diagram of a method of making a protein-PEG conjugate according to examples.

As illustrated in FIG. 2, examples may include a method 200 of making a protein-PEG conjugate with increased hydrophobicity. Method 200 may include providing an aqueous protein solution 202, which may include a protein and the pH buffer. The protein may be any protein previously described. The aqueous protein solution and the pH buffer may be any aqueous protein solution or pH buffer described herein.

Method 200 may further include reacting a polyethylene glycol with the protein to form a protein-PEG conjugate 204. The polyethylene glycol may have any molecular weight described herein. The protein may be any protein described herein. The reaction in forming the protein-PEG conjugate may proceed in any manner described herein. Method 200 may exclude protonating an amino group on the protein with a hydrophobic organic acid. Method 200 may not result in a protein-PEG conjugate salt.

Figure 3:
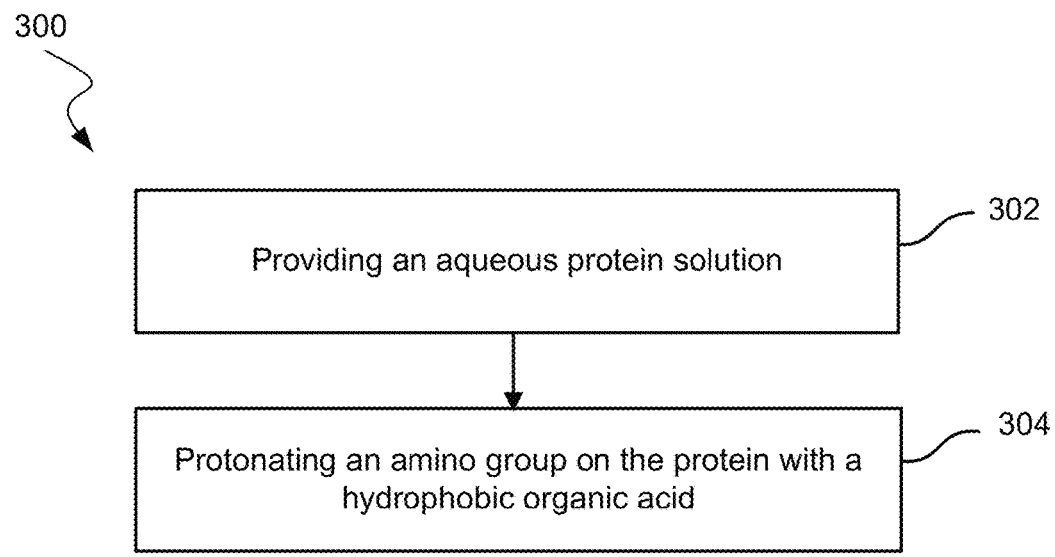
FIG. 3 shows a method of making a protein salt with increased hydrophobicity according to examples.
Figure 4:
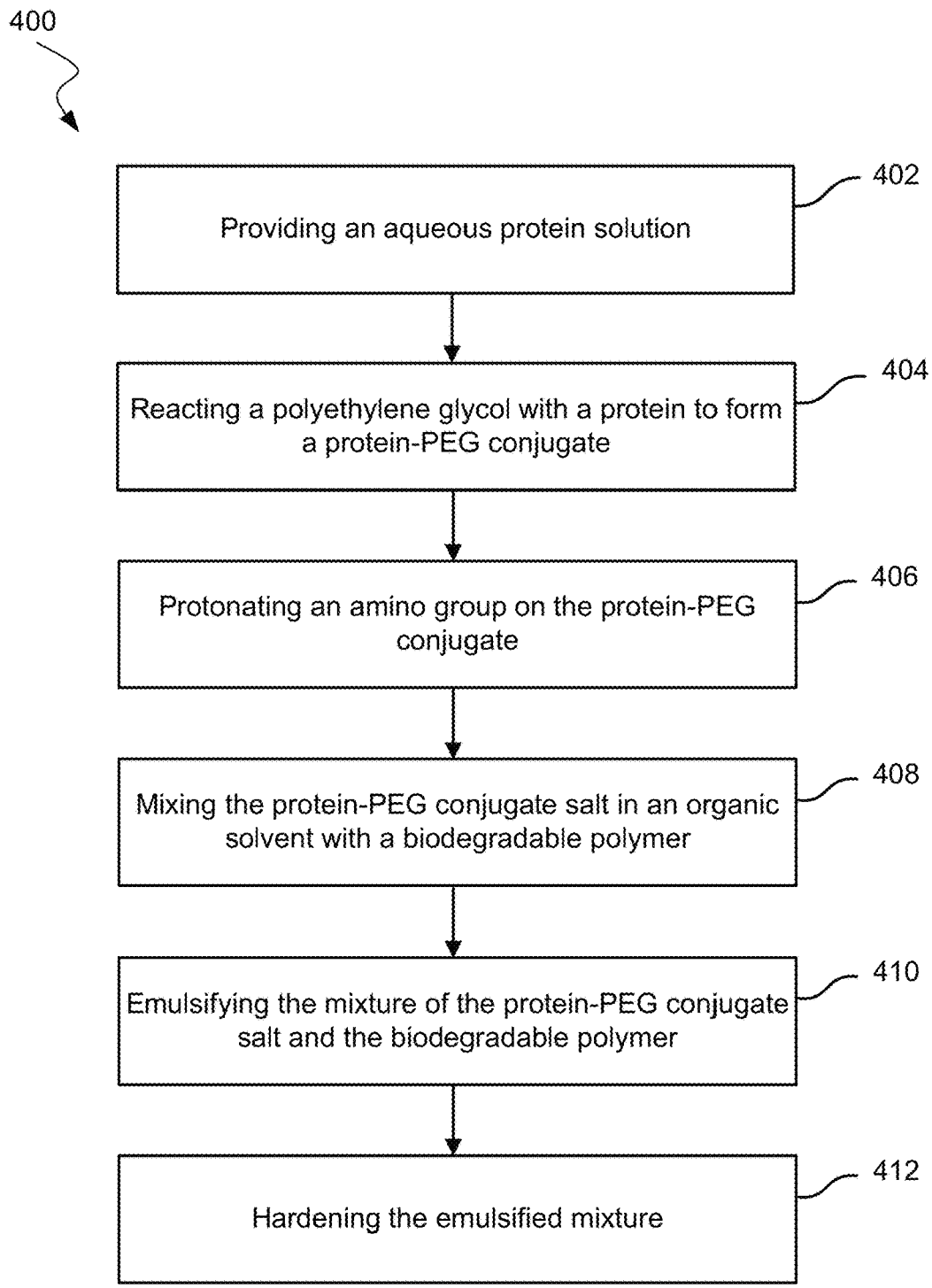
FIG. 4 shows a block diagram of a method of making controlled-release microspheres containing a protein-PEG conjugate salt according to examples.

Examples, as shown in FIG. 3, may include a method 300 of making a protein salt with increased hydrophobicity. Method 300 may include providing an aqueous protein solution 302 with a protein and a pH buffer. The protein may be separated from water. Method 300 may further include protonating an amino group on the protein with a hydrophobic organic acid 304. Protonating the amino group may occur in an organic phase and without the presence of water. The protonation may form the protein salt having a hydrophobic anion that increases the hydrophobicity of the protein salt. Method 300 may not include introducing the polyethylene glycol to the aqueous protein solution. Method 300 may not result in a protein-PEG conjugate or a protein-PEG conjugate salt. The aqueous protein solution, the protein, the pH buffer, the hydrophobic organic acid, and the hydrophobic anion may be any of the compounds previously described.

As in examples depicted in FIG. 4, a method 400 of making controlled-release microspheres containing a protein-PEG conjugate salt may include providing an aqueous protein solution 402. The aqueous protein solution may include a protein and a pH buffer. The protein may include any protein previously described. Method 400 may further include reacting a polyethylene glycol with the protein to form a protein-PEG conjugate 404. After the protein-PEG conjugate is formed, the protein-PEG conjugate may be separated from water. The protein-PEG conjugate may then be dissolved in an organic solvent.

In addition, method 400 may include protonating at least one amino group on the protein-PEG conjugate with a hydrophobic organic acid 406. The hydrophobic organic acid may be added to an organic phase and may not be added to an aqueous phase. Similarly, protonating the amino group may occur in the organic phase and without the presence of water. The protonation may form the protein-PEG conjugate salt having a hydrophobic anion. The hydrophobic organic acid may include any acid described herein, and the protein-PEG conjugate salt may be any conjugate salt described herein.

Furthermore, method 400 may include mixing the protein-PEG conjugate salt in an organic solvent with a biodegradable polymer 408. The organic solvent may be immiscible with an aqueous phase. The organic solvent may include methylene chloride, benzyl benzoate, dichloromethane, chloroform, ethyl ether, ethyl acetate, acetic acid isopropyl ester (isopropyl acetate), acetic acid sec-butyl ester, acetophenone, n-amyl acetate, aniline, benzaldehyde, benzene, benzophenone, benzyl alcohol, benzyl amine, bromobenzene, bromoform, n-butyl acetate, butyric acid methyl ester, caproic acid, carbon disulfide, carbon tetrachloride, o-chloroaniline, chlorobenzene, 1-chlorobutane, chloromethane, m-chlorophenol, m-cresol, o-cresol, cyanoethane, cyanopropane, cyclohexanol, cyclohexanone, 1,2-dibromoethane, dibromomethane, dibutyl amine, m-dichlorobenzene, o-dichlorobenzene, 1,1-dichloroethane, 1,2-dichloroethane, dichlorofluoromethane, diethyl carbonate, diethyl malonate, diethyl sulfide, diethylene glycol dibutyl ether, diisobutyl ketone, diisopropyl sulfide, dimethyl phthalate, dimethyl sulfate, dimethyl sulfide, N,N-dimethylaniline, enanthic acid, ethyl acetoacetate, ethyl benzoate, ethyl propionate, ethylbenzene, ethylene glycol monobutyl ether acetate, exxate 600, exxate 800, exxate 900, fluorobenzene, furan, hexamethylphosphoramide, 1-hexanol, n-hexyl acetate, isoamyl alcohol (3-methyl-1- butanol), isobutyl acetate, methoxybenzene, methyl amyl ketone, methyl benzoate, methyl formate, methyl isoamyl ketone, methyl isobutenyl ketone, methyl isobutyl ketone, methyl n-butyl ketone, methyl propyl ketone, 4-methyl-2-pentanol, N-methylaniline, nitrobenzene, nitroethane, 1-nitropropane, 2-nitropropane, 1-octanol, 2-octanol, 1-pentanol, 3-pentanone, 2-phenylethanol, n-propyl acetate, quinoline, styrene, 1,1,2,2-tetrachloroethane, 1,1,2,2-tetrachloroethylene, toluene, 1,1,1-trichloroethane, 1,1,2-trichloroethane, 1,1,2-trichloroethylene, trifluoromethane, valeric acid, m-xylene, o-xylene, p-xylene, 2,4-xylenol, or mixtures thereof. The organic solvent may exclude any solvent or any groups of solvents.

Methods may include a mixture of solvents. The mixture of solvents may include a solvent that is miscible in water, but the mixture of solvents may be immiscible in water. For examples, a water-miscible solvent such as dimethyl sulfoxide (DMSO), methanol, dimethylformamide (DMF), acetonitrile, tetrahydrofuran, or mixtures thereof may be added to the water immiscible solvent.

The biodegradable polymer may include a polylactide, a polyglycolide, a poly(d,l-lactide-co-glycolide), a polycaprolactone, a polyorthoester, a copolymer of a polyester and a polyether, or a copolymer of polylactide and polyethylene glycol. The biodegradable polymer may exclude any of these polymers or groups of these polymers. The molecular weight of the biodegradable polymer may be adjusted depending on the size of the PEG to produce a desired pharmacokinetic profile.

Poly(d,l-lactide-co-glycolide) (PLGA) may have a molecular weight from 5,000 Da to 7,000 Da, 7,000 Da to 17,000 Da, 17,000 Da to 20,000 Da, 20,000 Da to 24,000 Da, 24,000 Da to 38,000 Da, 38,000 Da to 40,000 Da, or 40,000 Da to 50,000 Da, in examples. PLGA may have a ratio of lactide to glycolide of 50:50 or 75:25. In some examples, PLGA may have a ratio of lactide to glycolide ranging from 40:60 to 50:50, from 50:50 to 60:40, from 60:40 to 70:30, from 70:30 to 75:25, or from 75:25 to 90:10. The ratio of lactide to glycolide may be less than or equal to 50:50, less than or equal to 60:40, or less than or equal to 75:25, where less than refers to a smaller proportion of lactide compared to glycolide. The hydrophobic anion of the organic acid may improve the release characteristics of some PLGAs but not others.

Possible PLGAs may include PLGA 502, PLGA 503, PLGA 752, and PLGA 753. PLGA 502 may be a polymer with a lactide to glycolide ratio of 50:50, an inherent viscosity from 0.16 to 0.24 dL/g, and a molecular weight from 7,000 to 17,000 Da. PLGA 503 may be a polymer with a lactide to glycolide ratio of 50:50, an inherent viscosity from 0.32 to 0.44 dL/g, and a molecular weight from 24,000 to 38,000 Da. PLGA 752 may be a polymer with a lactide to glycolide ratio of 75:25, an inherent viscosity from 0.14 to 0.22 dL/g, and a molecular weight from 4,000 to 15,000 Da. PLGA 753 may be a polymer with a lactide to glycolide ratio of 75:25, an inherent viscosity from 0.32 to 0.44 dL/g, and a molecular weight from 24,000 to 38,000 Da. The PLGA polymer may also be acid end-capped or ester end-capped.

The hydrophobic anion of the protein-PEG conjugate salt may increase the solubility of the salt in the organic solvent. Method 400 may also include emulsifying the mixture of the protein-PEG conjugate salt and the biodegradable polymer 410 in an aqueous solution. Additionally, method 400 may include hardening the emulsified mixture 412 of the protein-PEG conjugate salt and the biodegradable polymer into the controlled-release microspheres. The microspheres may include the hydrophobic anion of the organic acid. If an organic acid were added to an aqueous phase instead of an organic phase, the organic acid and any anions from the organic acid may not be included in a microsphere or may be included at a significantly lower concentration in the microsphere.

A method of making controlled-release microspheres may include a protein-PEG conjugate or a protein salt instead of a protein-PEG conjugate salt. The protein-PEG conjugate or the protein salt may be made by any method described herein.

Examples may include a microsphere with a biodegradable polymer. A microsphere may have a diameter under 1 mm. For example, the microsphere may have a diameter from 10 to 20 µm, 20 to 30 µm, 30 to 40 µm, 40 to 50 µm, 50 to 60 µm, 60 to 70 µm, 70 to 80 µm, 80 to 90 µm, or 90 to 100 µm. In addition, a plurality of microspheres may have a distribution where the microsphere diameter is in one of the ranges described herein. The diameter may be characterized by the mean, median (D50), 10 percentile (D10), or 90 percentile (D90) of the distribution. A microsphere that is too large may not be injectable with a syringe for treatment of an individual. Additionally, a microsphere that is too large may also delay the release of a medically active agent. On the other hand, if the diameter is too small, microspheres may be lost during processing, sieving, and/or screening.

The microsphere may further include a protein-polyethylene glycol conjugate, the protein and a hydrophobic anion of an organic acid, or mixtures thereof. The microsphere may also exclude a protein-polyethylene glycol conjugate or a hydrophobic anion of an organic acid. The protein may be any protein described herein. The composition may include a combination of proteins. For example, the composition may include GLP-1 and insulin. The GLP-1 and insulin may be present in a microsphere as part of a protein-PEG conjugate. The term premix may refer to a microsphere with a combination of proteins or protein-PEG conjugates. Alternatively, examples may include a postmix, which refers to a mixture of microspheres, where each microsphere may contain only one medically active agent but a combination of medically active agents may be included in the mixture of microspheres. The organic acid and the hydrophobic anion of an organic acid may be any compound previously described.

A composition may include a biodegradable polymer and may be presented as a microsphere. Microspheres may be prepared by first producing an emulsion from an aqueous solution and an immiscible solution, and may be followed by solvent extraction and drying. Emulsions may be produced by static mixing, dynamic mixing, or packed-bed emulsifiers.

Compositions with a biodegradable polymer may be solutions or suspensions in an organic solvent. These solutions may be delivered to the human body, and during the delivery, the organic solvent may dissolve in body fluid and may deposit the composition, including the biodegradable polymer. The organic solvent may be miscible with water and may not be toxic so the solvent may be injected into a patient. Additionally, in order to form a solution, a PEGylated protein, organic acid, and biodegradable polymer should dissolve in the organic solvent. For suspensions, at least one of the PEGylated protein, organic acid, and the biodegradable polymer should not be completely soluble in the organic solvent. Examples of organic solvents include N-methyl pyrrolidone, dimethyl sulfoxide, propylene glycol, ethyl benzoate, benzyl benzoate, triacetin, PEG 400, and mixtures thereof. The composition may exclude any organic solvent or groups of organic solvents. Examples of the present technology may include methods of making compositions with a biodegradable polymer in solution with an organic solvent.

Figure 5:
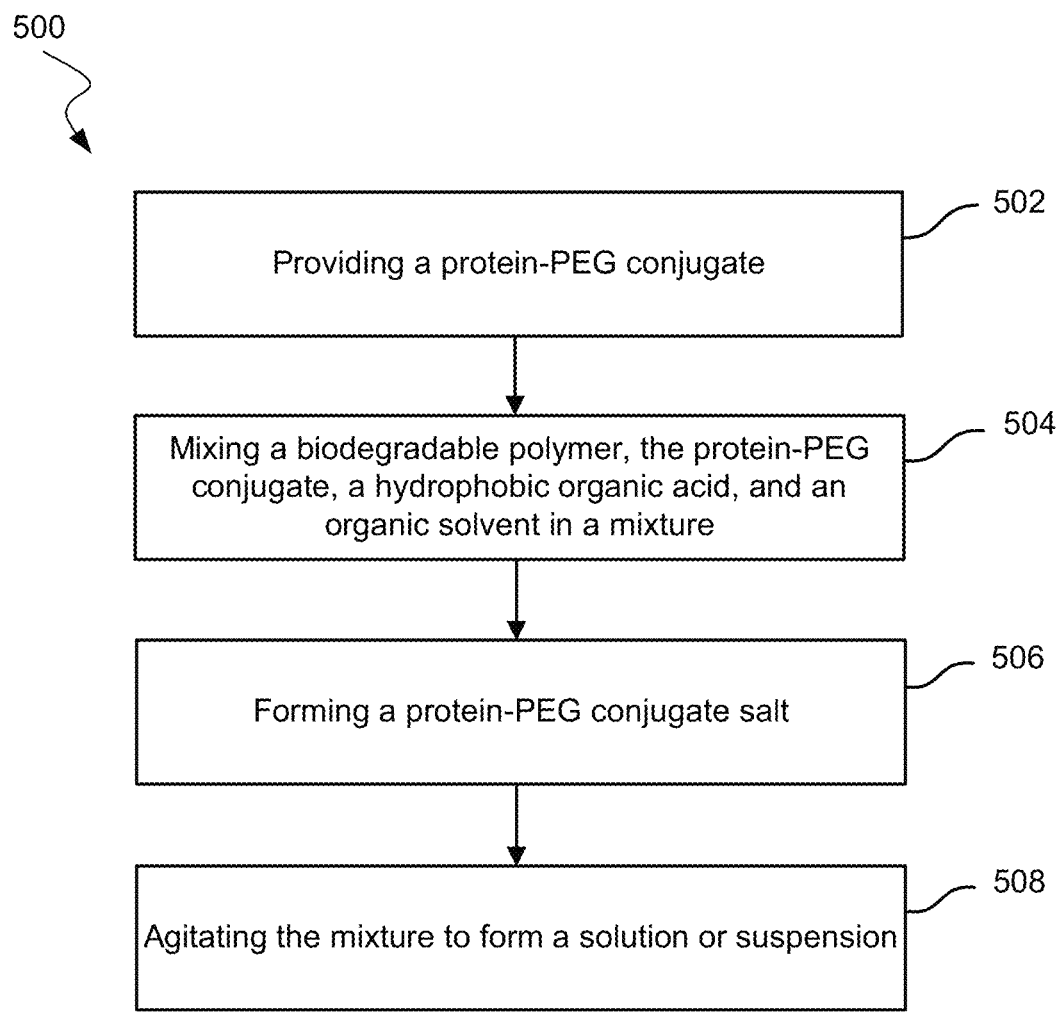
FIG. 5 shows a block diagram of a method of making a solution or suspension of a biodegradable polymer and a protein-PEG conjugate salt according to examples.

FIG. 5 shows a method 500 of making a solution or suspension of a biodegradable polymer and a protein-PEG conjugate salt. Method 500 may include providing a protein-PEG conjugate 502. Method 500 may also include mixing a biodegradable polymer, the protein-PEG conjugate, a hydrophobic organic acid, and an organic solvent in a mixture 504. The protein-PEG conjugate may be free of the protein-PEG conjugate salt. The protein-PEG conjugate may be glucagon-like peptide-1-PEG conjugate. Mixing may include mixing a second protein-PEG conjugate, which may be an insulin-PEG conjugate, in the mixture.

Additionally, method 500 may include forming the protein-PEG conjugate salt 506. The protein-PEG conjugate salt may include the protein-PEG conjugate and an anion of the hydrophobic organic acid. This conjugate salt may be formed concurrently with the dissolution of components in the organic solvent rather than providing an already formed salt and dissolving the salt in the solvent. Further, method 500 may include agitating the mixture to form the solution or suspension 508. The solution may be a clear solution after agitating. The protein-PEG conjugate, the biodegradable polymer, the hydrophobic organic acid, and the organic solvent may be any organic solvent described herein. Each component and each step may be free of water.

Figure 6:
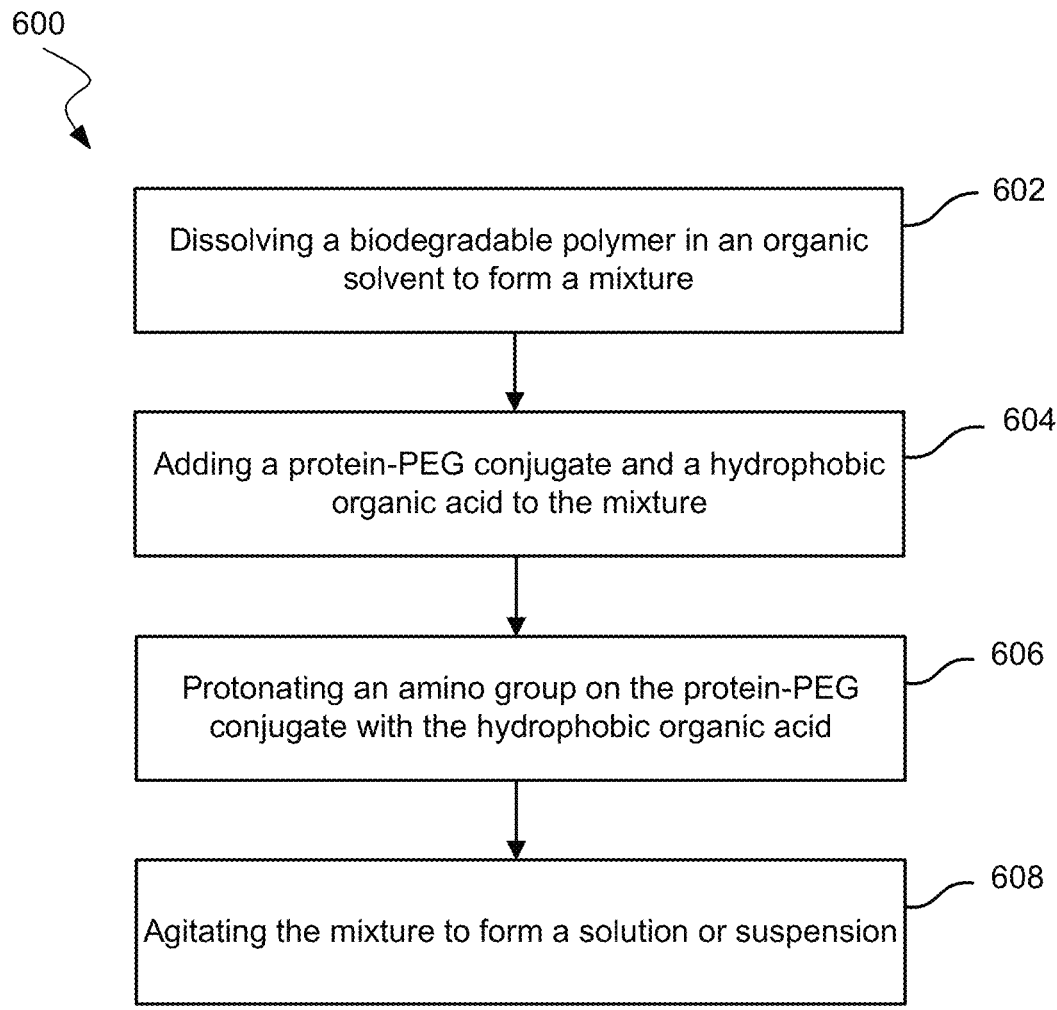
FIG. 6 shows a block diagram of a method of making a solution or suspension of a biodegradable polymer and a protein-PEG conjugate salt according to examples.

FIG. 6 shows a method 600 of making a solution or suspension of a biodegradable polymer and a protein-PEG conjugate salt. Method 600 may include dissolving a biodegradable polymer in an organic solvent to form a mixture 602. Method 600 may exclude dissolving a protein-PEG conjugate salt in the organic solvent. Method 600 may also include adding a protein-PEG conjugate and a hydrophobic organic acid to the mixture 604. Furthermore, method 600 may also protonating an amino group on the protein-PEG conjugate with a hydrophobic organic acid 606. The protonation may form the protein-PEG conjugate salt having a hydrophobic anion. Additionally, method 600 may include agitating the mixture to form the solution or suspension 608. The solution may be a clear solution after agitating. The protein-PEG conjugate, the biodegradable polymer, the hydrophobic organic acid, and the organic solvent may be any organic solvent described herein. Each component and each step may be free of water.

Solutions produced by method 500, method 600, or similar methods may produce a solution. The solution may be injected into an individual. When the solution contacts water, the solution may form a solid depot. The depot may then gradually release a protein or other medically active agent.

Example 1

The GLP-1 C-terminal cysteine mutein (GLP-1 [7-36] plus an added cysteine at position 37) was cloned as a fusion to a larger polypeptide that contained a self-cleaving autoproteolytic sequence between GLP-1 and its fusion partner. The fusion protein was expressed in *E. coli* using an IPTG inducible system under the control of T7 polymerase.

Example 2

The GLP-1 fusion protein was isolated from cell lysates under denaturing conditions, renatured, cleaved (autoproteolysis), and further purified using cationic chromatography. Characterization assays to confirm the peptides identity included RP-HPLC analysis, SDS-PAGE, and mass spectrometry. Commercially available synthetic cysteine mutein of GLP-1 was used as the control for these assays.

Example 3

The GLP-1 cysteine mutein (produced either by a recombinant or synthetic chemical process) was PEGylated with a 5 kDa or 10 kDa cysteine-reactive maleimide-PEG by the following process. The peptide was first dissolved in 20 mM sodium phosphate buffer, pH 7.5 at a concentration of 1-5 mg/mL, and an equal molar amount of the maleimide PEG reagent was added. The reaction was allowed to continue overnight. The PEGylated GLP-1 peptide was purified using cation exchange chromatography (SP-HP Sepharose) with an equilibration buffer of 10 mM sodium acetate at pH 3.5 and a step elution buffer of 0.02% ammonium bicarbonate. The product-containing fractions were pooled, dialyzed against 0.02% ammonium bicarbonate, and lyophilized. The concentration of purified PEGylated peptide was determined by UV spectroscopy or by Bradford protein assay. Additional analytical assays performed post-PEGylation include SEC-HPLC analysis, SDS-PAGE, mass spectral analysis, N-terminal analysis, and endotoxin determination. A larger PEG of 20 kDa was also tested. Even larger PEGs (e.g., 40 kDa branched) may also be tested.

Example 4

N-terminally PEG-GLP-1 was prepared by the following process. First, 30 mg of GLP-1 were dissolved in 20 mM sodium acetate at pH 4.5, reaching a GLP-1 concentration of 1 to 5 mg/mL. Next, 55 mg of 5-kDa propionadehyde PEG were added, followed by 2 mg of sodium cyanoborohydride. The reaction was allowed to continue overnight at room temperature. After 16 hours, the PEG-GLP-1 was purified by cation exchange chromatography (SP-HP Sepharose).

Example 5 hGH was subcloned in an *E. coli* IPTG inducible system under the control of T7 polymerase. Cells were grown to an OD600 nm=0.5, and 1 mM isopropyl-β-D-thiogalactopyranoside IPTG was added to induce expression. The induced culture was incubated overnight for about 16 hr. The cells were pelleted by centrifugation and stored at −20° C.

The cell pellet was thawed, suspended in lysis buffer (1 mM EDTA, 150 mM NaCl, 50 mM Tris, 1% Triton X-100, pH 7.5) and homogenized by three passages thru a microfluidizer. Insoluble material was recovered by centrifugation, suspended in salt buffer (500 mM NaCl, 50 mM Tris, pH 7.5), and again collected by centrifugation. The insoluble pellet (inclusion bodies) was stored at −20° C.

A portion of the insoluble pellet (~15 mg hGH) was thawed, dissolved in 10 mL of 8 M urea, 10 mM cysteine, 20 mM BisTris, stirred for 60 min at room temperature, and then diluted into 100 mL of 20 mM Tris, 15% glycerol, pH 8.5. The refold mixture was held at 4° C. for 1 day, centrifuged, and loaded onto a 5 mL Q-Sepharose XL column equilibrated in 20 mM BisTris, pH 7.0 (Buffer A). The bound proteins were eluted with a pH/salt gradient (0-100%) with Buffer B (50 mM NaCl, 20 mM BisTris, pH 5). Column fractions were analyzed by RP-HPLC analysis, and fractions containing renatured hGH were pooled and stored at −20° C.

Example 6

Refolded, purified hGH was N-terminally PEGylated by the following protocol. First, 30 mg of hGH were first dissolved in 20 mM sodium acetate, pH 4.5, reaching an hGH concentration of 5 mg/mL. Next, 40 mg of 10-kDa propionadehyde PEG were added followed by 8 mg of sodium cyanoborohydride. The reaction was allowed to continue overnight at room temperature. After 16 hours, the PEG-hGH was purified using a 5 mL Q-Sepharose HiTrap column.

Example 7

GLP-1-loaded PLGA microspheres with a hydrophobic counter ion were prepared by the following process. First, 30 mg of 5 kDa-PEG-GLP-1 were dissolved in 2 mL of dichloromethane. Next, 50 µL of a pamoic acid solution (50 mg/mL in dimethyl formamide [DMF]) were added. PLGA 502 at 170 mg was next added to the peptide solution and mixture was vortexed until clear. Afterwards, 5 mL of an emulsion stabilizer (1% polyvinyl alcohol [PVA]) were added, and the mixture was immediately vortexed at the max speed on a Genie vortexer for 7-8 sec. At that point, the emulsion was quickly added to 100 mL of 0.3% PVA while rapidly stirring. After 10 min, 150 mL of 2% isopropanol was added, and the suspension was stirred for 3-12 hours to allow for solvent evaporation and microsphere hardening. The resulting microspheres were isolated by settling, washed three times with 200 mL purified water, and lyophilized. Different PLGA polymers were used to prepare weekly (e.g., PLGA 502) or monthly formulations (e.g., PLGA 753) of microspheres including GLP-1 and pamoic acid.

Example 8

Verification of the drug and hydrophobic ion loading of the microspheres is accomplished by first dissolving the microspheres in acetonitrile, followed by precipitation of the polymer by diluting with water. The resulting supernatant is analyzed by RP-HPLC. The analysis showed that PEG-GLP-1 loaded microspheres containing pamoic acid were produced with drug loadings ranging from 2% to 18% for PEG-GLP-1 and around 0.3% to 0.5% pamoic acid. RP-HPLC results confirmed that pamoic acid was incorporated into the microspheres.

Example 9

Figure 7A:
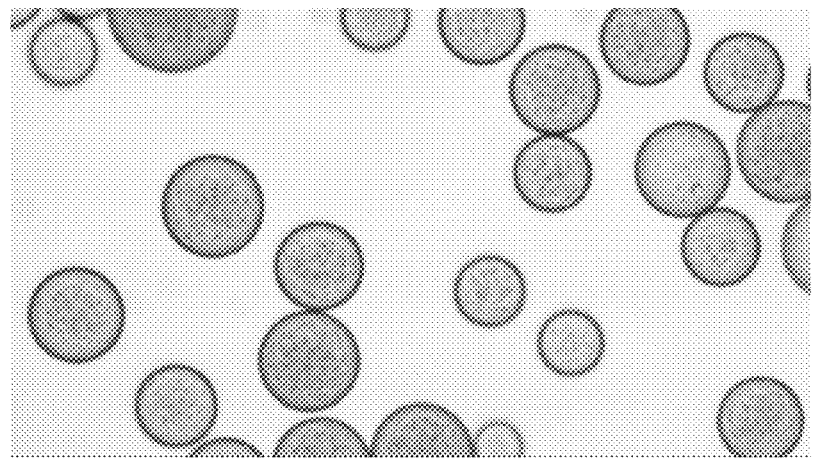
FIGS. 7A and 7B show light microscopy images of PLGA microspheres loaded with medically active agents.
Figure 7B:
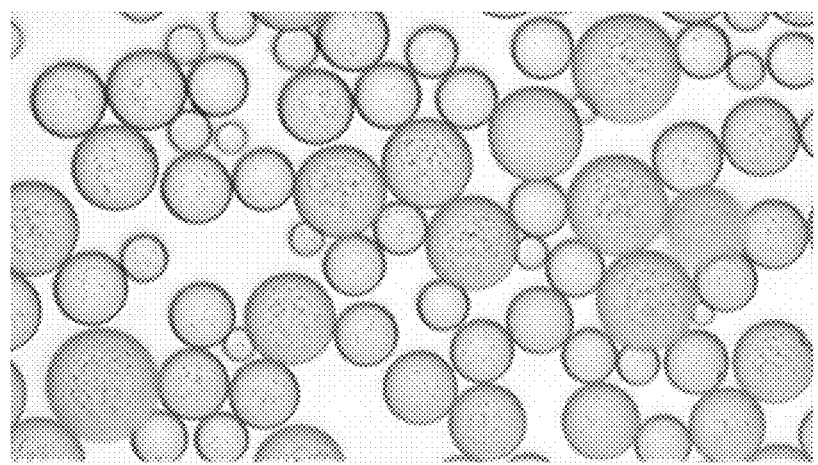

Particle sizes were measured using a Beckman particle analyzer. The particles had mean diameters between 20 and 45 µm, which is a range that can be conveniently dosed subcutaneously using a 27 gauge syringe. The particles examined by light microscopy show smooth spheres with minimal surface artifacts or inclusions. The particles also have fewer surface artifacts and inclusions than some conventional particles with medically active agents. FIG. 7A shows light microscopy images of PLGA 502 microspheres loaded with PEG-GLP-1 with pamoic acid. The particles in FIG. 7A have a D10 of 16 µm, a D50 of 33 µm, and a D90 of 50 µm. FIG. 7B shows light microscopy images of PLGA 502 microspheres loaded with a premix of PEG-insulin and PEG-GLP-1 and pamoic acid. The particles in FIG. 7B have a D10 of 18 µm, a D50 of 30 µm, and a D90 of 42 µm. The particle sizes measured show a tight distribution around a syringeable diameter.

Example 10

For initial burst release studies, microspheres were prepared with 170 mg of various PLGA polymers, 30 mg of PEG-GLP-1, and 50 µL of a pamoic acid solution (50 mg/mL in dimethyl formamide [DMF]). Control microspheres were also prepared with PLGA, PEG-GLP-1, and with and without 50 µL DMF. The microspheres, after freeze drying, were suspended in 0.4% PVA plus 0.05% sodium azide and incubated at 37° C. with rotisserie-like mixing. After 24 hours, the suspensions were centrifuged, and the supernatant analyzed by RP-HPLC with the amount of released PEGylated peptide quantified based on standard curves. Table 1 shows percentages of the total PEGylated peptide initially present in the microspheres. A lower initial burst percentage may be generally desired in treatments. Based on the data in Table 1, the pamoic acid minimized the initial burst of PEG-GLP-1 from microspheres that were produced using PLGA polymers with a molecular range around 12-18 kDa (PLGA 502 and PLGA 752). For microspheres with PLGA 503, pamoic acid increased the burst. Table 1 also shows that the change in the burst amount was likely a result of the pamoic acid and not the DMF solvent.

TABLE 1

Effect of pamoic acid on the burst percentage from microspheres prepared with different PLGAs

| PLGA | No Additive | Pamoic acid + DMF | DMF |
|---|---|---|---|
| 502 | 24.5 | 1.2 | 15.4 |
| 503 | 0 | 8.5 | 0 |
| 752 | 24 | 4.6 | 18.2 |
| 753 | 0 | 0 | 0 |

Example 11

Figure 8:
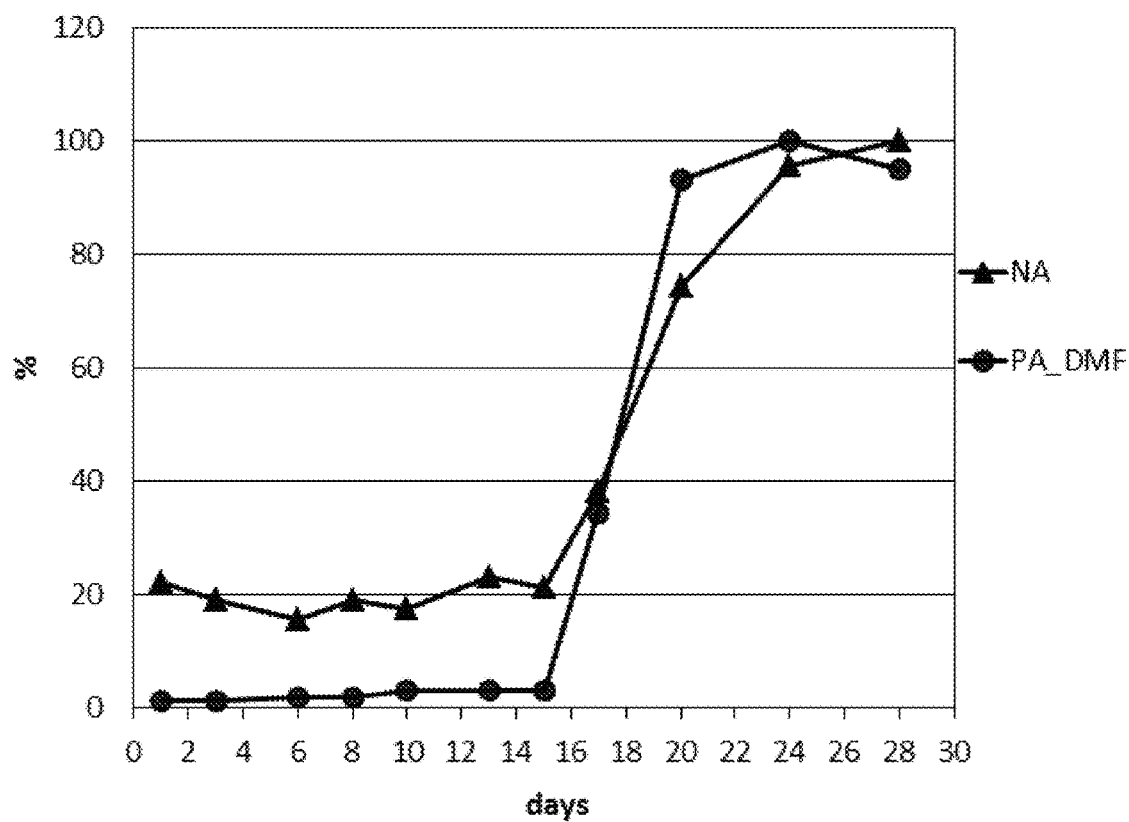
FIG. 8 shows a graph of results of an extended release study on microspheres according to examples.
Figure 9:
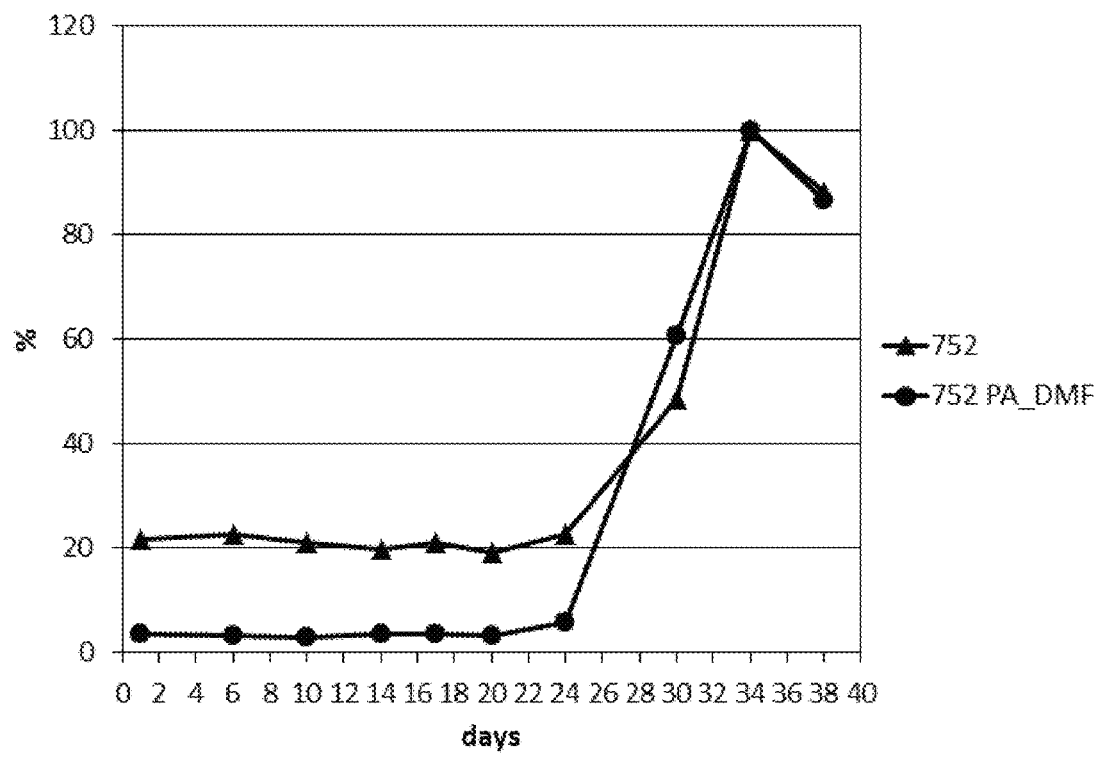
FIG. 9 shows a graph of results of an extended release study on microspheres according to examples.

For the extended release studies, microspheres were prepared with 170 mg of various PLGA polymers, 30 mg of PEG-GLP-1, and 50 µL of a pamoic acid solution (50 mg/mL in dimethyl formamide [DMF]). Control microspheres were also prepared with PLGA, PEG-GLP-1, and with and without 50 µL DMF. The microspheres, after freeze drying, were suspended in 0.4% PVA and 0.05% sodium azide and incubated at 37° C. with rotisserie-like mixing. After specific time points, the suspensions were centrifuged, and the supernatant analyzed by RP-HPLC with the amount of released PEGylated peptide quantified based on standard curves. FIGS. 8 and 9 show graphs of results of these extended release studies on microspheres. The figures show release values as percentages of the total PEGylated peptide initially present in the microspheres. FIGS. 8 and 9 show that pamoic acid minimized the initial release of PEG-GLP-1 but had little effect on the final release profile. Rather, the timing of the full release was mostly dependent on the hydrophobicity of the PLGA polymer. PLGA 502 has a 50:50 ratio of lactide to glycolide, and PLGA 752 has a 75:25 ratio of lactide to glycolide. A higher ratio of lactide to glycolide results in a more hydrophobic PLGA polymer. Accordingly, PLGA 752 took longer to release PEG-GLP-1 than PLGA 502.

Example 12

Biacore (GE Healthcare) studies were performed to measure the in vitro binding affinities of the PEGylated GLP-1 compounds for the GLP-1 receptor. The GLP-1 receptor was covalently immobilized to the biosensor surface, and the PEGylated GLP-1 compound or GLP-1 was injected over the surface. The equilibrium dissociation constants ($K_D$) for GLP-1 receptor binding were 1.6 µM for 5 kDa-PEG-GLP-1 (Cys analog), and the $K_D$ was 1.0 µM for unmodified GLP-1. The equilibrium constant for N-terminal 5 kDA-PEG-GLP-1 could not be determined, likely as a result of extremely weak interaction between the receptor and the N-terminal PEGylated peptide. Attaching a PEG polymer to the C-terminus may not significantly affect the specific activity of GLP-1 whereas attaching a PEG polymer to the N-terminus may interfere with receptor binding.

Example 13

The in vitro bioactivities of the PEGylated GLP-1 conjugates were measured in a cell-based assay GLP-1 receptor binding assay using CHO-K1/GLP1/Gal5 and monitoring the GLP-1-induced concentration-dependent stimulation of intracellular calcium mobilization. The cells were loaded with Calcium-4 prior to stimulation with a GLP-1 receptor agonist. The intracellular calcium change was measured by FlexStation. The relative fluorescent units (RFU) were plotted against the log of the cumulative doses (5-fold dilution) of GLP-1. Table 2 shows $EC_{50}$, the concentration at which 50% of the highest activity level is reached. A lower $EC_{50}$ indicates a higher activity. In agreement with the Biacore data of Example 12, C-terminally PEGylated GLP-1 showed close to full activity compared to the unmodified GLP-1 peptide. The 5 kDa PEG for the C-terminally PEGylated GLP-1 did not appear to significantly affect the activity. The specific activities of the N-terminally PEGylated GLP-1 peptides were significantly reduced compared to the C-terminally PEGylated GLP-1. Using a 2 kDa PEG instead of a 5 kDa PEG for N-terminally PEGylated GLP-1 was not observed to significantly affect the activity.

TABLE 2

GLP-1 receptor binding data

| Compound | $EC_{50}$ (M) |
|---|---|
| GLP-1 (7-36) | $3.80 \times 10^{-7}$ |
| 5 kDa-PEG-Cys(37)-GLP-1 | $3.36 \times 10^{-7}$ |
| 5 kDa-PEG-N-term-GLP-1 | $1.3 \times 10^{-5}$ |
| 2 kDa-PEG-N-term-GLP-1 | $3.41 \times 10^{-5}$ |

Example 14

Dual peptide loaded microspheres containing the PEG-GLP-1, PEG-insulin, and pamoic acid were prepared using an oil/water single-emulsion solvent extraction/evaporation process. The oil phase consisted of 170 mg of PLGA polymer, 10 mg of PEG-insulin, 20 mg of PEG-GLP-1, and 2.5 mg of pamoic acid (from a pamoic acid stock of 50 mg/mL in DMF) dissolved in 2 mL of dichloromethane. The oil phase was emulsified by vortexing with 5 mL of 1% w/v PVA, and the primary emulsion was added to a 100 mL of 0.3% PVA stirring at 300 rpm. Then 150 ml, of 2% IPA was added approximately 10 minutes later, and the suspension was stirred to facilitate solvent evaporation. After 3 hours, the hardened microspheres were washed three times with 200 mL purified water and freeze dried.

Example 15

Figure 10:
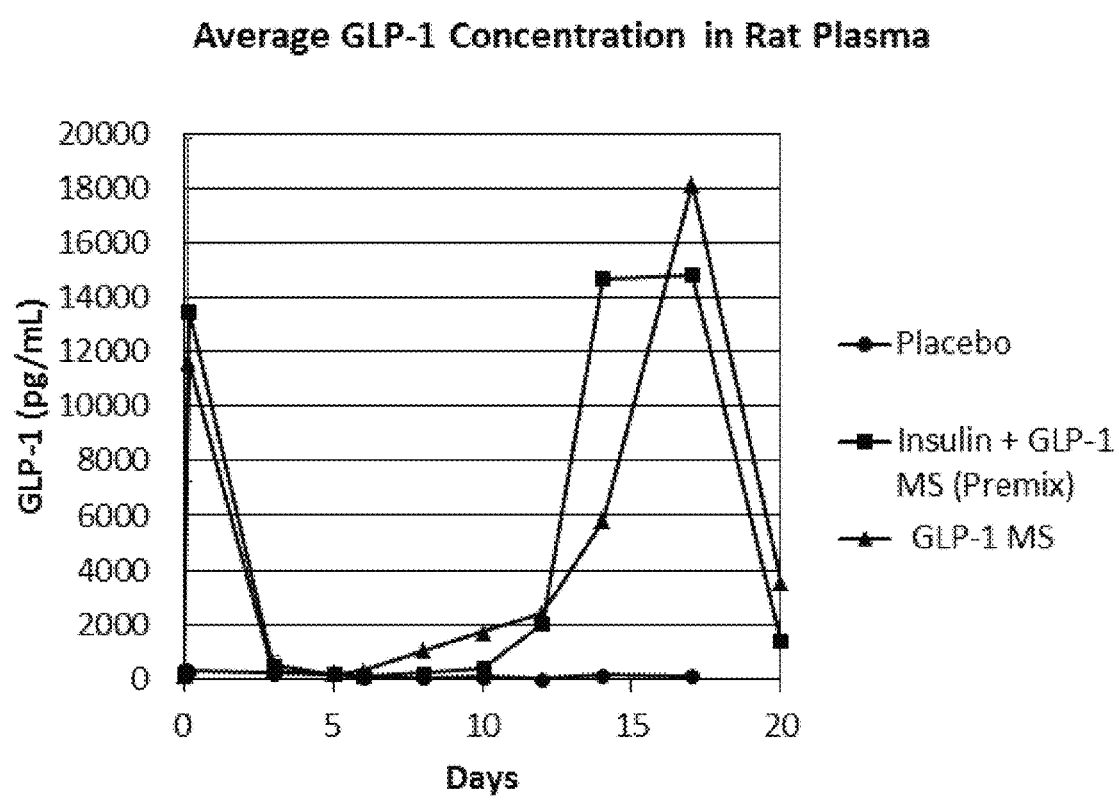
FIG. 10 shows pharmacokinetic analysis of GLP-1 in rat plasma samples after microsphere dosing according to examples.
Figure 11:
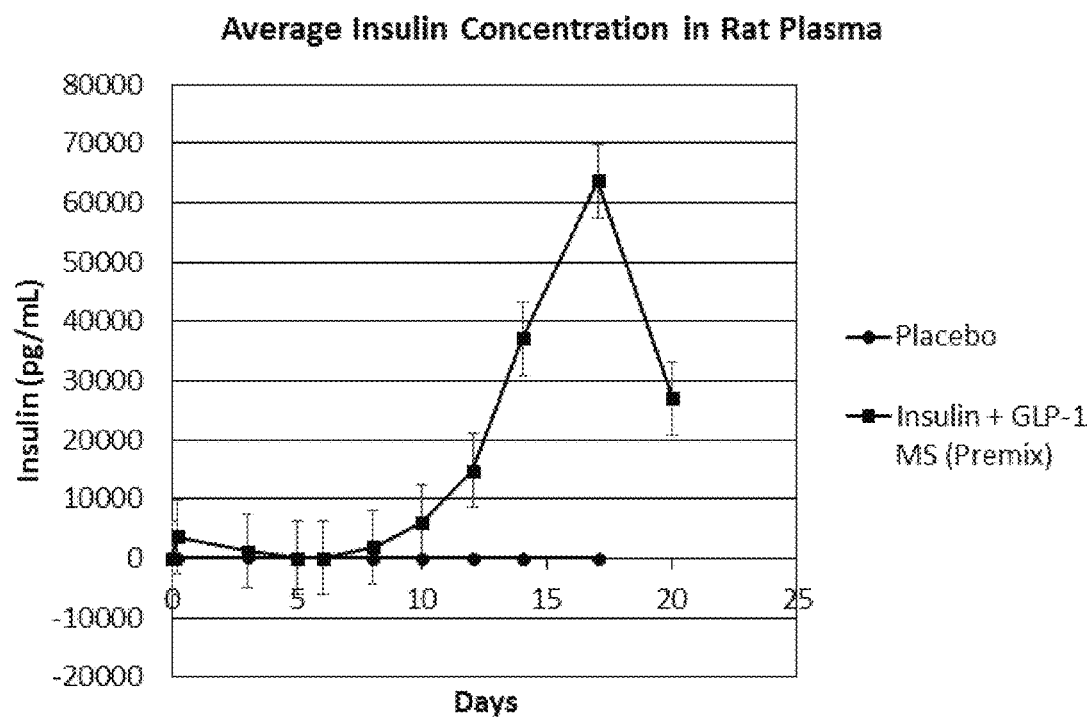
FIG. 11 shows pharmacokinetic analysis of insulin in rat plasma samples after microsphere dosing according to examples.

Pharmacokinetic studies were performed in a 20 day study with Sprague Dawley male rats. The rats (6 per group) were each given a subcutaneous injections of either PEG-GLP-1 loaded microspheres (MS) or dual loaded PEG-GLP-1 and PEG-insulin microspheres (premix). Both the PEG-GLP-1 MS and the premix contained pamoic acid and PLGA 502. An additional control included a placebo group, which was diluent only (sodium carboxymethycellulose [1%], D-mannitol [5%] and polysorbate 20 [0.1%]). The in vivo release profile was determined by collection of the plasma samples at predetermined time points followed by ELISA analysis of the samples (EM Millipore Anti-GLP-1 kit). FIGS. 10 and 11 show the pharmacokinetic analyses of GLP-1 or insulin in rat plasma samples after microsphere dosing. In both cases, the PEGylated peptides were released in vivo with a peak concentration occurring at around 17 days. The GLP-1 release profile was not observed to be significantly affected by including PEG-insulin. The release of insulin with the premix microspheres occurred at about the same time as the GLP-1. Thus, premix microspheres were observed to release medically active agents at about the same time as non-premix microspheres.

Example 16

PLGA microspheres containing enfuvirtide and pamoic acid were prepared using an o/w single-emulsion solvent extraction/evaporation process. Enfuvirtide was not PEGylated. The oil phase consisted of 170 mg of PLGA 502, 30 mg of enfuvirtide, 8 mg of pamoic acid and 2 mL of dichloromethane. The oil phase was emulsified using vortexing with 5 mL of 1% w/v PVA, and the primary emulsion was added to a 100 mL of 0.3% PVA stirring at 300 rpm. Then 150 mL of 2% IPA were added approximately 10 minutes later, and the suspension was stirred to facilitate microsphere hardening. After 3 hours, the hardened microspheres were filtered, washed with a large volume of double distilled $H_2O$, and freeze dried. A second lot of microspheres were also prepared as described above in this example except pamoic acid was not added to the mixture. Particle size analysis of the enfuvirtide microspheres prepared with pamoic acid present displayed greater homogeneity (mean size: 28 µM; S.D: 9.5 µM) versus the enfuvirtide microspheres without pamoic acid (mean size: 32.75 µM; S.D: 34.07 µM).

Example 17

In situ formulations were prepared containing PLGA, PEG-GLP-1, pamoic acid, and N-methyl pyrrilidone (NMP). First, 340 mg of PLGA (either PLGA 503, PLGA 752, or PLGA 753) were dissolved in 1 mL of N-methyl pyrrolidone (NMP). Next, 30 mg of PEG-GLP-1 were added along with 2.5 mg of pamoic acid (from a stock of 200 mg/mL in DMSO). The mixtures were swirled gently until clear. For release, each solution was loaded into a dialysis cassette (Slide-A-lyzer 3.5 kDa cutoff) and suspended in a beaker of 900 mL of phosphate buffered saline and 0.05% polysorbate. The dialysis buffer was gently stirred overnight at room temperature. After 16 hours at room temperature, depots had formed within the cassettes with a layer of liquid on top. The liquid and solids were separated, and PEG-GLP-1 content was determined by RP-HPLC analysis. The calculated burst for the individual depots was 11% for the PLGA 503 polymer, 62% for the PLGA 752 polymer, and 40% for the PLGA 753 polymer. The burst was observed to be affected by the hydrophobicity of the PLGA polymer.

Example 18

In situ formulations were prepared containing PLGA, PEG-GLP-1, pamoic acid, and a mixture of FDA-approved solvents. First, 340 mg of PLGA 752 were dissolved in 1 mL of a mix of 50% N-methyl pyrrolidone (NMP) and 50% benzyl benzoate or a mix of 50% DMSO and 50% benzyl benzoate. Next, 30 mg of PEG-GLP-1 were added along with 2.5 mg of pamoic acid (from a stock of 200 mg/mL in DMSO). The mixture was swirled gently until clear. For release, each solution was loaded into a dialysis cassette (Slide-A-lyzer 3.5 kDa cutoff) and suspended in a beaker of 900 mL of phosphate buffered saline and 0.05% polysorbate. After 16 hours at room temperature, depots had formed within the cassettes with a layer of liquid on top. The liquid and solids were separated, and PEG-GLP-1 content was determined by RP-HPLC analysis. The calculated burst for the DMSO:benzyl benzoate mixture was 2.6% versus 0.2% for the NMP:benzyl benzoate based in situ formulation. DMSO is more polar than NMP. The desired rate of release (weekly versus monthly dosing) may be adjusted based on the based on the hydrophobicity and concentration of the PLGA, the water miscibility of the solvent(s), and/or the addition of pamoic acid.

Example 19

Examples 1-18 are repeated with human growth hormone, insulin, enfuvirtide, parathyroid hormone, a fragment of PTH, octreotide, or other medically active agent in place of GLP-1, insulin, and/or enfuvirtide. Examples may also include preparing microspheres and compositions with organic solvents for any of the compositions in Examples 1-19. These examples showed superior concentration profiles and other characteristics compared to conventional compositions and methods.

In this description, for the purposes of explanation, numerous details have been set forth in order to provide an understanding of various examples of the present technology. It will be apparent to one skilled in the art, however, that certain examples may be practiced without some of these details, or with additional details.

Having described several examples, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific example may not always be present in variations of that example or may be added to other examples.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the protein" includes reference to one or more proteins and equivalents thereof known to those skilled in the art, and so forth. The invention has now been described in detail for the purposes of clarity and understanding. However, it will be appreciated that certain changes and modifications may be practice within the scope of the appended claims.

The invention claimed is:

1. A microsphere comprising:
    a biodegradable polymer selected from the group consisting of a polylactide; a polyglycolide; a poly(d,l-lactide-co-glycolide); a polycaprolactone; a polyorthoester; a copolymer of a polyester and a polyether; and a copolymer of polylactide and polyethylene glycol; and
    a protein mixture selected from the group consisting of a protein-polyethylene glycol conjugate and a hydrophobic anion of an organic acid, a protein and the hydrophobic anion of the organic acid, and combinations thereof, wherein the organic acid comprises pamoic acid, docusate hydrogen, furoic acid, or mixtures thereof;
    and wherein the microsphere is formed by a process comprising:
        adding the organic acid to the protein-polyethylene glycol conjugate or the protein in a water-immiscible solvent in an organic phase to form a water-immiscible solution, wherein the addition occurs without the presence of water.

2. The microsphere of claim 1, wherein the protein of the protein-polyethylene glycol conjugate or the protein comprises human growth hormone.

3. The microsphere of claim 1, wherein the protein of the protein-polyethylene glycol conjugate or the protein comprises glucagon-like peptide-1.

4. The microsphere of claim 3, further comprising an insulin-polyethylene glycol conjugate.

5. The microsphere of claim 1, wherein the protein of the protein-polyethylene glycol conjugate or the protein is selected from the group consisting of insulin, parathyroid hormone, a fragment of parathyroid hormone, enfuvirtide, and octreotide.

6. The microsphere of claim 1, wherein:
    the protein mixture comprises the protein-polyethylene glycol conjugate, and
    the polyethylene glycol of the protein-polyethylene glycol conjugate comprises methoxy polyethylene glycol.

7. The microsphere of claim 1, wherein:
    the protein mixture comprises the hydrophobic anion of the organic acid, and
    the organic acid comprises pamoic acid, and the hydrophobic anion comprises a pamoate anion.

8. The microsphere of claim 1, wherein:
    the protein mixture comprises the protein-polyethylene glycol conjugate and the hydrophobic anion of the organic acid, and
    a molar ratio of the hydrophobic anion of the organic acid to the protein-polyethylene glycol conjugate ranges from 1:1 to 11:1.

9. The microsphere of claim 1, wherein:
    the protein mixture comprises the protein-polyethylene glycol conjugate, and
    the protein-polyethylene glycol conjugate comprises a monoPEGylated conjugate.

10. The microsphere of claim 1, wherein the biodegradable polymer comprises poly(d, l-lactide-co-glycolide).

11. The microsphere of claim 1, wherein the biodegradable polymer has a molecular weight from 7,000 Da to 17,000 Da.

12. A method of making controlled-release microspheres containing a protein-PEG conjugate salt; the method comprising:

provviding an aqueous protein solution comprising a protein and a pH buffer;

reacting a polyethylene glycol with the protein to form a protein-PEG conjugate;

protonating an amino group on the protein-PEG conjugate with a hydrophobic organic acid in a water-immiscible solvent in an organic phase without the presence of water to form a water-immiscible solution, wherein the protonation forms the protein-PEG conjugate salt having a hydrophobic anion;

mixing the protein-PEG conjugate salt in an organic solvent with a biodegradable polymer to form a mixture, wherein:

the hydrophobic anion of the protein-PEG conjugate salt increases the solubility of the protein-PEG conjugate salt in the organic solvent, the biodegradable polymer is selected from the group consisting of a polylactide; a polyglycolide; a poly(d,l-lactide-co-glycolide); a polycaprolactone; a polyorthoester; a copolymer of a polyester and a polyether; and a copolymer of polylactide and polyethylene glycol, and the organic acid comprises pamoic acid, docusate hydrogen, furoic acid, or mixtures thereof;

emulsifying the mixture of the protein-PEG conjugate salt and the biodegradable polymer in an aqueous solution to form an emulsified mixture; and hardening the emulsified mixture of the protein-PEG conjugate salt and the biodegradable polymer into the controlled-release microspheres.

13. The method of claim 12, wherein the hydrophobic organic acid comprises pamoic acid.

14. The microsphere of claim 1, wherein:

the protein mixture comprises the protein-polyethylene glycol conjugate and the hydrophobic anion of the organic acid, and a molar ratio of the hydrophobic anion of the organic acid to the protein-polyethylene glycol conjugate ranges from 3:1 to 8:1.

15. The microsphere of claim 1, wherein the hydrophobic anion has a water-octanol partition coefficient log P greater than 1.

16. The microsphere of claim 1, wherein the process further comprises protonating at least one amino group on the protein or the protein-polyethylene glycol conjugate.

* * * * *